United States Patent [19]

Bauer et al.

[11] Patent Number: Plant 7,701

[45] Date of Patent: Nov. 5, 1991

[54] VARIETY OF STRAWBERRY NAMED FLORIKA

[75] Inventors: Annelise Bauer, Hechlstrasse 11, D-8211 Breitbrunn; Birgit Schlindwein, Freising, both of Fed. Rep. of Germany

[73] Assignee: Annelise Bauer, Fed. Rep. of Germany

[21] Appl. No.: 478,641

[22] Filed: Feb. 12, 1990

[51] Int. Cl.[5] ..... A01H 5/00

[52] U.S. Cl. ..... Plt./48

[58] Field of Search ..... Plt./48

[56] References Cited

PUBLICATIONS

Scott, D. H., et al., "Strawberries" *Advances in Fruit Breeding* Janick, J., et al. (eds) Purdue University Press, West Lafayette, Indiana 1975, pp. 71–95.

Bauer, R., "New Patterns of Heterosis in Fragaria Hybrids" *Eucarpia* VII (1976) pp. 63—68.

*Primary Examiner*—James R. Feyrer

*Attorney, Agent, or Firm*—Webb, Burden, Ziesenheim & Webb

[57] ABSTRACT

A *vescana* type strawberry plant characterized by its capability of developing exceptionally rich and fine flavor of medium sized fruits. The plant is best suited for to pick for your own cultivations as well as for house gardens. The cultivar does not need extensive care and forms meadow-type fields of densely growing and randomly distributed plants.

4 Drawing Sheets

DESCRIPTION

This invention relates to a new and distinct decaploid *Fragaria vescana* hybrid designated as cultivar Florika and derived from the combination of the hexaploid F1-hybrid×168.7 ("Sparkle"×*F. vesca semperflorens*) crossed with the octoploid *F. ananassa* variety Hummi. The cultivar Florika was originally designated Florina.

Florika as an amphidiploid decaploid *vescana* hybrid does combine 8 genoms of *F. ananassa* (garden strawberry) and 2 genoms of *F. vesca semperflorens* (wild strawberry). The decaploid of *vescana*-hybrids has been determined by counting the chromosomes (2n=70).

The variety is asexually reproduced by taking runners from mother plants. The cut runners are planted into the soil where they take root and develop to young plants in the usual manner. The variety has been found to retain its distinctive characteristics from generation to generation since 1985.

Florika first fruited at the Institut for Obstbau der Technischen Universitat Munchen-Weiehnstephan in 1987. It was tested later as an advanced selection. The variety is a *vescana*-type strawberry plant characterized by its capability of developing exceptionally rich and fine flavor of medium sized fruits. The plant is best suited for "pick your own" cultivations as well as for house gardens. The cultivar does not need extensive care and forms meadow-type fields of densely growing and randomly distributed plants.

SOURCE OF THE PLANT

The parents of 'Florika' were arrived at by a cross between a *vesca* type *Fragaria semperflorens* which had been treated with colchicine to double its chromosome number to be compatably crossed with an ananassa hybrid 'Sparkle', 'Sparkle' itself having resulted from a cross between *F. chiloensis*×*virginiana*. This cross resulted in a highly sterile hexaploid which was backcrossed to 'Sparkle'. The hybrid from the cross was crossed with 'Hummi' resulting in the claimed plant, *Florika', a classic vescana* hybrid decaploid genome, which is fertile and productive. The complex of the breeding program has been reported by Mr. R. Bauer in "New Patterns of heterosis in Fragaria hybrids" *Eucarpia VII* (1976), pages 63–68, incorporated herein by reference.

IN THE DRAWINGS

THE PLANT

Figure 1:
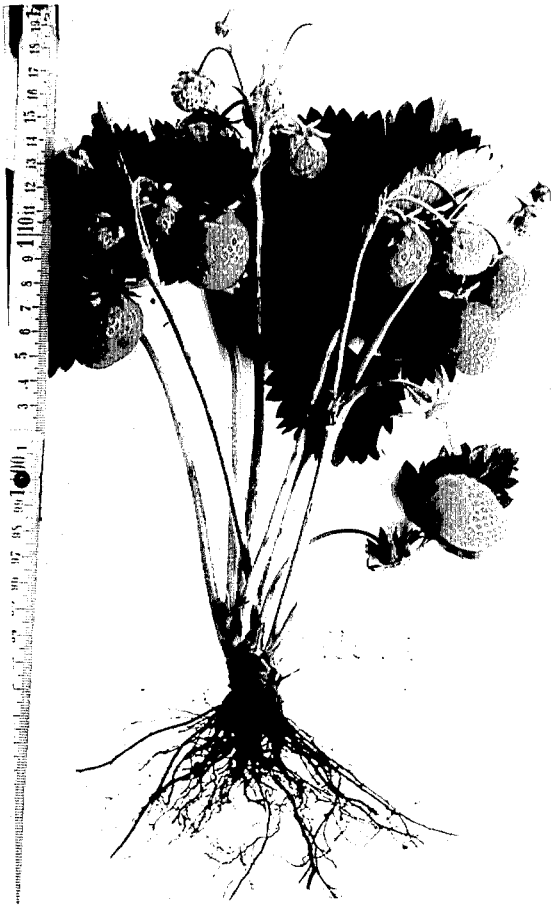
FIG. 1 is a photograph showing an individual plant bearing fruit, the height of the plant above the soil is about 10 inches.
Figure 2:
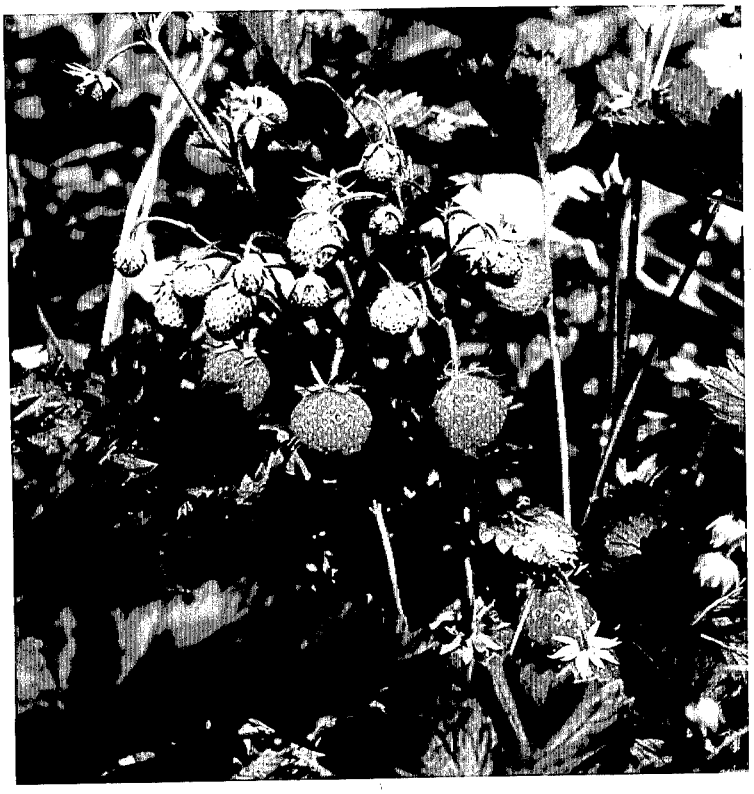
FIG. 2 is a photograph showing a typical plant in a meadow-type field with typical growth, flowering and fruiting characteristics.
Figure 3:
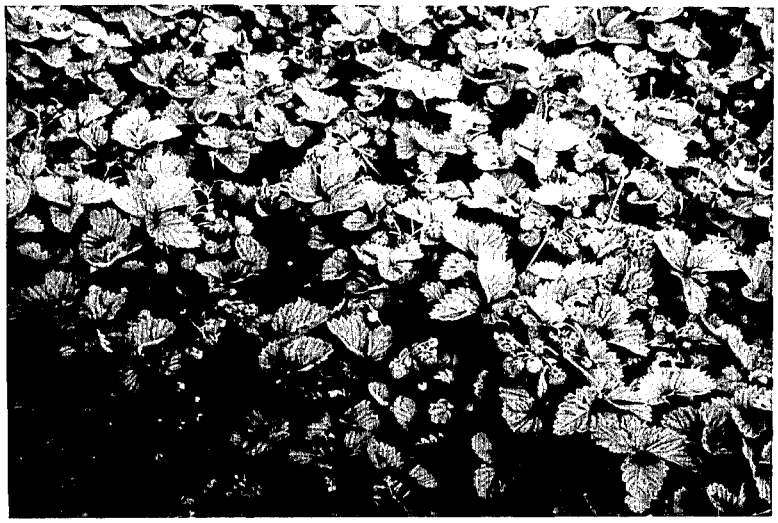
FIG. 3 is a photograph showing a meadow-type culture in the second year after planting.
Figure 4:
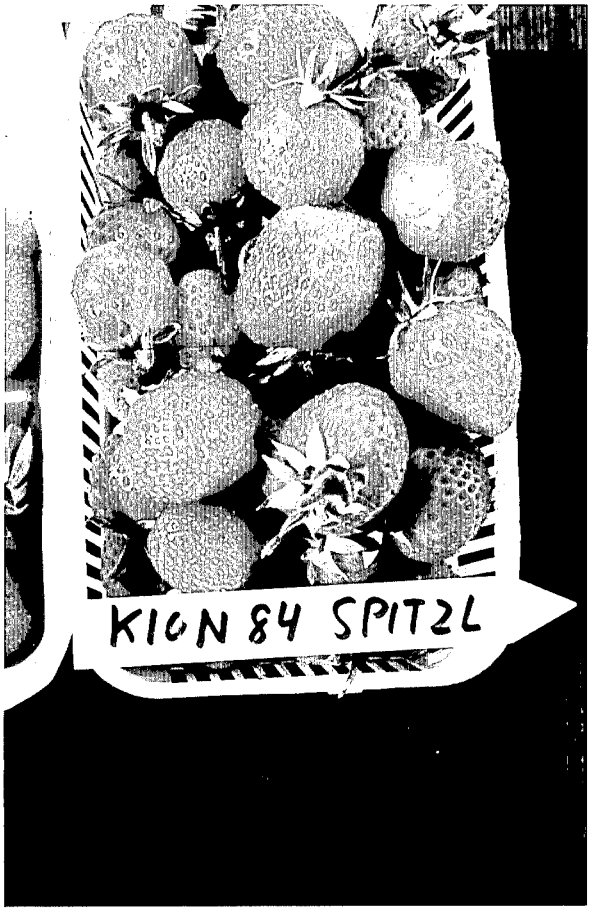
FIG. 4 is a photograph showing a small basket full of harvested strawberries Florika.

Classification: *Fragaria vescana*-hybrids.

Leaf:

*Middle leaflet.*—Length/width ratio: broader than long.

*Terminal leaflet size.*—2–4 inches long.

*Shape of base.*—Between acute and obtuse.

*Color.*—Dark green.

Petiole:

*Poise of hairs.*—Outwards.

Inflorescence:

*Position relative to foliage.*—Above.

*Description.*—The flowers are medium large with 5–6petals. The petals are broader than long. Calyx sepals are the same size or larger as compared to the petals.

Fruit:

*Predominant shape.*—Oblate.

*Size.*—15–30 mm (0.59–1.18 inches) in diameter.

*Color.*—Red Group 43B, R.H.S.

*Insertion of achenes.*—Below surface.

*Time of ripening.*—Medium early.

*Type of bearing.*—Not remontant.

*Internal fruit color.*—Orange-red (not even).

*Firmness.*—Medium.

Seeds:

*Fertility.*—Hermaphrodite and self-fertile.

*Description.*—The fertile seeds are oval and of medium size, reddish-yellow, mostly below to even with surface of fruit.

The leaves are similar in size to those of *Fragaria×ananassa;* terminal leaves are approximately 1–4 inches long, they are nearly hairless on the upper side and have few hairs on the under side, on the ribs thereof. The terminal leaflets are obtuse to acute in contrast to the more elliptical leaves of the parent plants and are 0.2–0.4 inches long. Side leaflets are slightly smaller. Inflorescences are upright and have 5 to 12 blossoms with hairy stalks and they remain upright even when bearing fruit. The petals remain in close contact with the body of the berry, which, when ripe, may have a diameter of approximately 1 inch ±⅛. Petals are appoximately ½ inch long and seem slightly longer than those of Spadeka.

GROWTH CHARACTERISTICS

Florika demonstrates a heterosis growth which is typical of the *vescana* strawberry varieties, and which is characterized by a strong production of runners in the first years resulting in a dense meadow which can be used as a "meadow-culture" without the need of further cultivation of the soil and plants. The strawberry-meadow can exist for many years, contrary to the short-living, row-type culture of the garden strawberries. The individual plants in the strawberry meadow-type culture have strong leaf stalks, and fruit clusters and healthy medium green leaves. As a rule, 2 to 3 clusters per plant are formed and bear 10 to 12 berries. On maturity they are held rather visible mainly by the dense leaf crowns at foliage-height distance from the ground. Only in the first year when the meadow is growing is the control of weeds necessary, either by mechanical means as in house gardens or by herbicidal means as in fields cultivated on a commercial scale. In the second year, when the meadow is dense and yields fruit, weeds can no longer grow and make the use of agents for destroying vermin practically superfluous. After the harvest and wilting of the leaves, the field can be, but need not be, mowed a few inches above ground. Runners which only develop at the edge of the field once the meadow is dense, may be trimmed if an extension of the meadow is not desirable. Planting new plants is carried out from mid-September to October and in spring. New plants should be spaced approximately 1 foot apart.

FRUIT CHARACTERISTICS

The time of ripening is medium early. The time of ripening is related to Germany, where the harvest season for strawberries lasts from mid-June to the end of July. Florika ripens at the same time as the varieties Elsanta and Tenira and about 1 to 2 days earlier than the *vescana* variety Spadeka. Although the beginning and ending of the ripening season varies from year-to-year and from location-to-location, nevertheless, the respective time of ripening of the different varieties relative to one another usually does not vary.

The harvesting period is longer as compared to the *vescana* variety Spadeka. The berries are large to medium large (15 to 30 mm, 0.59 to 1.18 inches, in diameter) and small towards the end of the harvesting period in accordance with the insertion sequence. They are attractive, medium-red and can be easily picked. They may be picked off above the calyx with a small stalk. Therefore, despite their relatively soft flesh, they are more stable in transportation than the Spadeka variety. Removing them from the calyx later can be easily done. The berries have rose fruit flesh and develop a fine and very aromatic flavor. They have a balanced ratio of sugar to acidity and are suitable for all final uses both in fresh and deep frozen form. The consistency of the flesh is medium firm.

Investigations have been made at the Federal Research Centre of Nutrition, Institute of Chemistry and Biology, Karsruhe. Compared with 11 octoploid cultivars, Florika achieved the best results in respect of high flavor and aromatic smell. The taste is "wild strawberry-like".

DISEASES AND PESTS

Botrytis susceptibility is so low that spraying is not required. Nor is there, as a rule, other protective sprayments against other diseases or pests required. As in the closed meadow-type culture, an ecologically balanced subculture develops. Resistance against mildew and blight is excellent.

CULTIVATION VALUE

For the one who has a garden and who wishes to harvest without much work, unsprayed berries with an excellent flavor for several years, a *vescana* strawberry meadow with Florika is an enrichment.

For commercial cultivation, Florika is of interest to growers for self-picking (pick your own), as cultivation in the field allows high yields with little work and care over many years. Cultivating the soil and placing straw under the plants is not required. The consumer will welcome and appreciate above all that the plants and berries need not be sprayed with pesticides and fungicides, etc.

I claim:

1. The new distinct variety of *vescana* strawberry plant named Florika as herein described and illustrated.

* * * * *

UNITED STATES PATENT AND TRADEMARK OFFICE

CERTIFICATE OF CORRECTION

PATENT NO. : Plant 7,701

DATED : November 5, 1991

INVENTOR(S) : Annelise Bauer and Birgit Schlindwein

It is certified that error appears in the above-identified patent and that said Letters Patent is hereby corrected as shown below:

TITLE PAGE

Abstract Line 3 after "suited" delete --for--.

Column 1 Line 20 "for" should read --fur--.

Delete paragraph following "SOURCE OF PLANT" and insert the following: --The grandparents of "Florika" were arrived at by a cross between a Fragaria vesca type semperflorens which had been treated with colchicine to double its chromosome number to be compatibly as a tetraploid plant crossed with an octoploid F. ananassa cultivar "Sparkle". This cross resulted in a highly sterile hexaploid hybria x168.7. This hybrid was crossed with the ananassa cultivar "Hummi" resulting in the claimed plant. "Florika" represents a decaploid vescana hybrid with ten genomes which is fertile and productive. The complex of the breeding program has been reported by Mr. R. Bauer in "New Patterns of heterosis in Fragaria hybrids" Eucarpia VII (1976), pages 63-68, incorporated herein by reference.--

Column 2 Line 32 "5-6petals" should read --5-6 petals--.

Signed and Sealed this

Fourth Day of January, 1994

*Attest:*

Bruce Lehman

BRUCE LEHMAN

*Attesting Officer*

*Commissioner of Patents and Trademarks*